United States Patent
Kronich et al.

(10) Patent No.: US 7,322,832 B2
(45) Date of Patent: Jan. 29, 2008

(54) RADIO FREQUENCY ANTENNA FLEXIBLE CIRCUIT INTERCONNECT WITH UNIQUE MICRO CONNECTORS

(75) Inventors: Christine G. Kronich, St. Paul, MN (US); Todd H. Schaefer, Blaine, MN (US); Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 481 days.

(21) Appl. No.: 10/973,137

(22) Filed: Oct. 26, 2004

(65) Prior Publication Data

US 2006/0089682 A1    Apr. 27, 2006

(51) Int. Cl.
*H01R 12/00* (2006.01)
(52) U.S. Cl. .......................... 439/67; 439/909; 607/36; 607/37
(58) Field of Classification Search .............. 439/67, 439/77, 909; 607/36, 37
See application file for complete search history.

(56) References Cited

U.S. PATENT DOCUMENTS

| 6,171,138 | B1 * | 1/2001 | Lefebvre et al. ............ 439/500 |
| 6,352,434 | B1 * | 3/2002 | Emmert ........................ 439/65 |
| 6,498,951 | B1 * | 12/2002 | Larson et al. ................. 607/36 |

* cited by examiner

*Primary Examiner*—Tho D. Ta
(74) *Attorney, Agent, or Firm*—Daniel G. Chapik (57) ABSTRACT

An RF antenna flexible circuit interconnect is disclosed with unique micro connectors. The RF antenna flexible circuit interconnect further includes a planer flexible body having an embedded RF transmission line with a first end and a second end. A first antenna micro connector is electrically coupled to the first end of the RF transmission line and a second antenna micro connector is electrically coupled to the second end of the RF transmission line. Each of the first and second antenna micro connectors include an antenna micro connector housing and an antenna central contact socket securely positioned within the antenna micro connector housing. The antenna central contact socket may also include inward bending fingers and may be designed to engage a pin that is inserted into the central contact socket.

20 Claims, 7 Drawing Sheets

RADIO FREQUENCY ANTENNA FLEXIBLE CIRCUIT INTERCONNECT WITH UNIQUE MICRO CONNECTORS

TECHNICAL FIELD

This invention relates generally to implantable medical devices (IMDs) having radio frequency (RF) telemetry capabilities for transmitting (uplink) patient data and receiving (downlink) programming and interrogation commands to and from an external programmer or other medical device, and more particularly, to a radio frequency antenna flexible circuit interconnect between an RF module located within an IMD housing and an antenna feedthrough for an RF telemetry antenna located outside the IMD housing.

BACKGROUND

A wide variety of implantable medical devices (IMDs) that employ electronic circuitry for providing electrical stimulation of body tissue and/or monitoring a physiologic condition are known in the art. IMDs may include implantable pulse generators (IPG), cardiac pacemakers, pacemaker-cardioverter-defibrillators, nerve, muscle and neurological stimulators, cardiomyostimulators, implantable drug dispensers, implantable cardiac signal monitors and recorders, and the like. IMDs typically include a housing that encloses a variety of internal components and isolates them from the implanted environment. IMDs may include integrated circuits, charging capacitors, batteries, and other components that are enclosed in hermetically sealed metallic housings. Within the human body, for example, the housing must be sealed to prevent ingress of fluids that can cause the device to short circuit or corrode internal components, which renders the IMD inoperable.

The IMDs typically comprise a hermetically sealed housing containing the battery and electronic circuitry. Many IMDs are capable of two-way communication or telemetry between the IMD and an external device, (e.g., a programmer). For example, in a pacemaker system, a programmer downloads data to an implanted pacemaker such as operating parameters. Likewise, data may flow in the opposite direction; that is, from the implanted pacemaker to the programmer for analysis. In fact, modern IMD's are capable of storing significant amounts of data about the patient (e.g., average heart rate) and the pacemaker itself (e.g., battery voltage), which may need to be frequently transmitted to the programmer or other device for evaluation by the physician.

One way of communicating with an IMD is through RF telemetry transmission, which relies upon magnetic field coupling through the patient's skin of an IMD IPG antenna with a closely spaced programmer antenna or broadcast telemetry over a greater distance from the IMD to a receiver. The RF telemetry antenna is positioned outside the hermetically sealed IMD housing, which allows it to operate in a high frequency RF telemetry bandwidth and reduces space requirements inside the housing. The RF telemetry antenna is connected to an antenna feedthrough. RF telemetry circuitry on an RF module is positioned inside the hermetically sealed IMD housing. The RF module must be coupled to the antenna feedthrough. This can be a problem due to the positioning of the RF module in relation to the antenna feedthrough and the small amount of space inside the housing.

Accordingly, it is desirable to provide a flexible radio frequency (RF) antenna flexible circuit interconnect between an RF module inside an IMD housing and an antenna feedthrough for an RF telemetry antenna located outside the IMD housing. Furthermore, other desirable features and characteristics of the present invention will become apparent from the subsequent detailed description and the appended claims, taken in conjunction with the accompanying drawings and the foregoing technical field and background.

BRIEF SUMMARY

An apparatus is provided for a flexible radio frequency (RF) antenna flexible circuit interconnect attaching between an RF module inside an IMD housing and an antenna feedthrough. The RF antenna flexible circuit interconnect, further includes unique micro connectors.

The micro connectors include a micro connector housing and a central contact socket securely positioned within the micro connector housing. The central contact socket may include inward bending fingers and may be designed to engage a pin that is inserted into the central contact socket. The micro connector housing and central contact socket are made of electrically conductive material.

An RF antenna flexible circuit interconnect is disclosed that includes a planar flexible body having an embedded RF transmission line having a first end and a second end. A first antenna micro connector is electrically coupled to the first end of the RF transmission line and a second antenna micro connector is electrically coupled to the second end of the RF transmission line. A ground member is electrically coupled to the flexible body and may be positioned near the second antenna micro connector. The first antenna micro connector is designed to electrically couple with an antenna pin of an RF module and the ground member and the second antenna micro connector are designed to electrically couple with an antenna feedthrough.

An implantable medical device is disclosed that includes a hermetically sealed housing with an antenna feedthrough having an antenna pin and an antenna ground, an RF module positioned within the hermetically sealed housing having an antenna pin, and an RF antenna flexible circuit interconnect coupling the antenna feedthrough and the RF module. The RF antenna flexible circuit interconnect includes a planer flexible body with an embedded RF transmission line having a first end and a second end. A first antenna micro connector is electrically coupled to the first end of the RF transmission line and a second antenna micro connector is electrically coupled to the second end of the RF transmission line. A ground member is electrically coupled to the flexible body and may be positioned near the second antenna micro connector. The first antenna micro connector is designed to electrically couple with the antenna pin of an RF module, the second antenna micro connector is designed to electrically couple with the antenna pin, and the ground member is designed to electrically couple with the antenna ground of the antenna feedthrough.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

For the sake of brevity, conventional techniques related to signal processing, data transmission, and other functional aspects of the RF systems (and the individual operating components of the RF systems) may not be described in detail herein.

The present invention will be described in relation to a particular IMD design using RF telemetry, but it is not intended that the invention be limited to any particular design when it can be advantageously implemented in various types of IMDs, such as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc.

Figure 1:
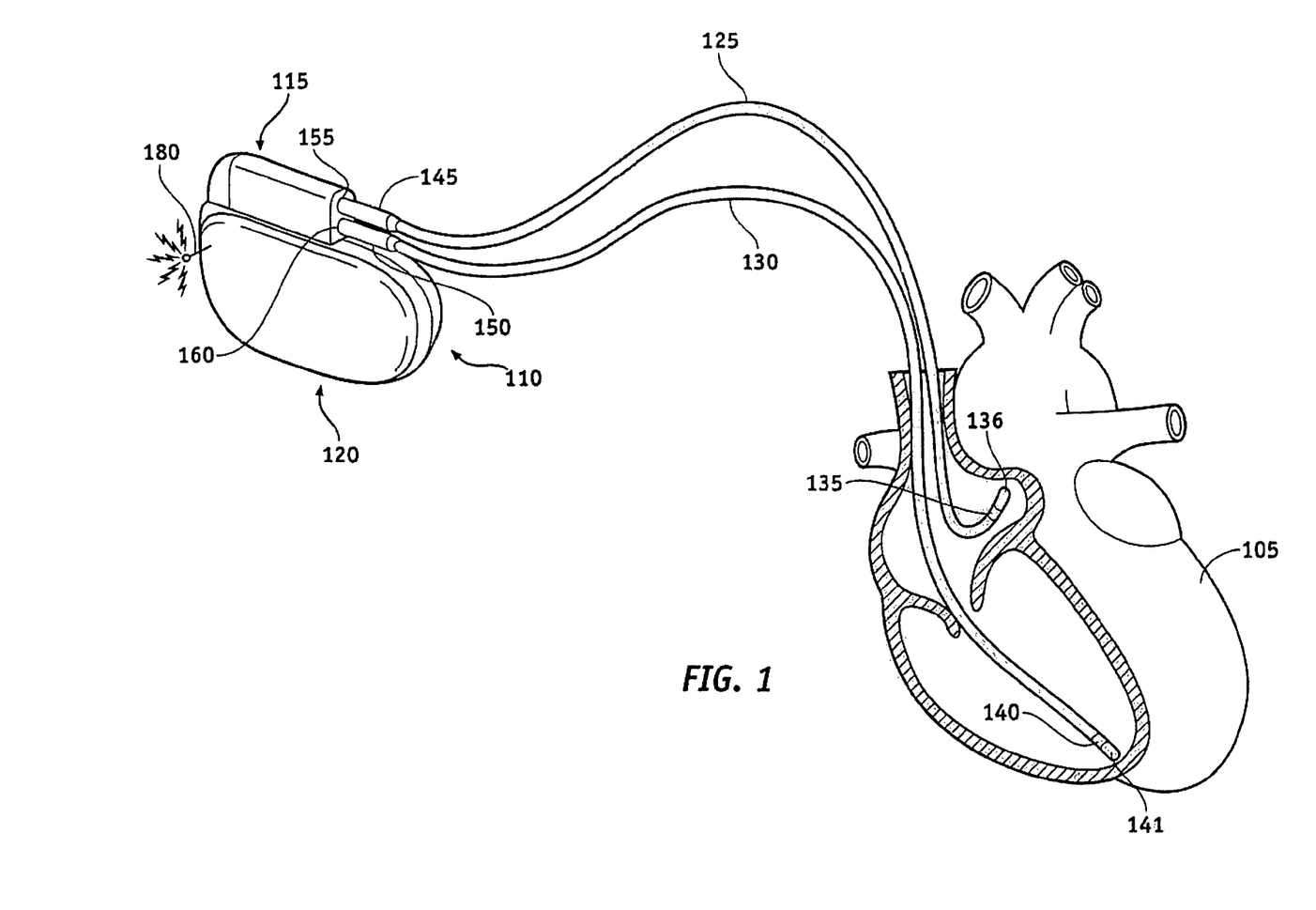
FIG. 1 is a simplified schematic view showing an implantable medical device in relation to a human heart.

FIG. 1 depicts an implantable medical device (IMD) 110, shown as a dual chamber pacemaker IPG, as it relates to patient's heart 105. The IMD 110 includes a connector header 115 and a hermetically sealed enclosure 120. Atrial and ventricular pacing leads 125 and 130 extend from the connector header 115 to the right atrium and ventricle, respectively. Atrial electrodes 135 and 136 disposed at the distal end of the atrial pacing lead 125 are located in the right atrium. Ventricular electrodes 140 and 141 at the distal end of the ventricular pacing lead 130 are located in the right ventricle.

The connector header 115 establishes electrical and mechanical connections of proximal connector end assemblies 145 and 150 of the atrial and ventricular pacing leads 125 and 130 to electrical or electronic circuitry disposed within hermetically sealed enclosure 110. Connector header 115 therefore preferably incorporates connector blocks (not shown) within the connector header housing that are aligned with elongated lead connector end receptacles 155 and 160, and that are adapted to receive lead connector end assemblies 145 and 150. Any other lead, fixation mechanism, and/or electrode configuration known in the art may be used with the current invention, and those shown are exemplary only. Feedthroughs and feedthrough pins connected to the connector blocks and extending through the hermetically sealed enclosure 120 are not shown in FIG. 1. Connector header 115 may be molded of a rigid thermoplastic material such polyurethane, polysulfone or any other such suitable medical grade thermoplastic material.

While atrial and ventricular pacing leads are shown in FIG. 1, other leads are contemplated at other locations in the body that may monitor and/or deliver therapy. For example, other embodiments may include neuro leads for neuro therapy systems; drug leads drug delivery systems; stimulation leads for stimulation therapy systems; sensor leads for monitoring activity; or other compatible monitor and/or treatment delivery leads for other systems.

The IMD 110 also includes a IMD RF telemetry antenna 180 electrically coupled to the telemetry circuitry on an RF module using a radio frequency antenna flexible circuit interconnect with unique micro connectors, discussed below. The IMD RF telemetry antenna 180 may by any compatible RF telemetry antenna, such as a surface mounted antenna. In one embodiment, the IMD RF telemetry antenna 180 is incorporated into the connector header.

Figure 2:
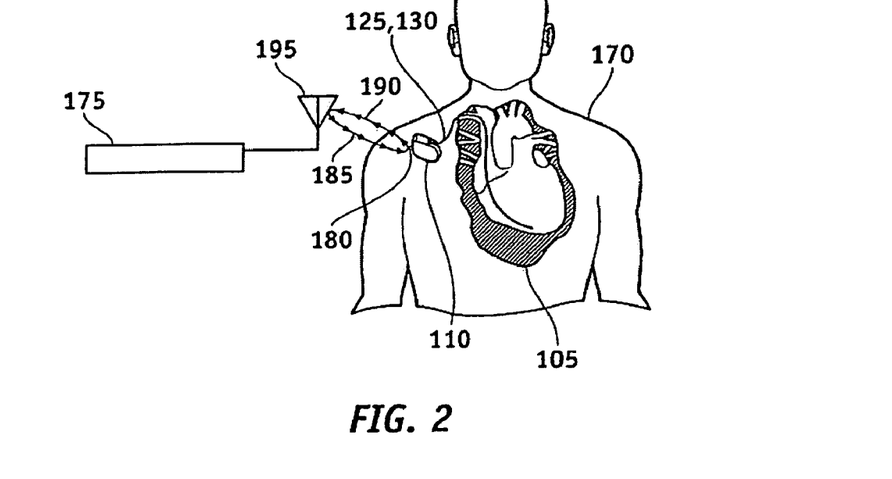
FIG. 2 is a simplified schematic view of the implantable medical device communicating with an external device by RF telemetry.

FIG. 2 illustrates RF telemetry communication between the IMD 110 and an external device 175, such as a programmer. While a dual chamber pacemaker IPG is shown, other IMDs would communicate similarly. The IMD 110 is implanted in the patient 170 beneath the patient's skin or muscle. The IMD 110 is electrically coupled to the heart 105 of the patient 170 through pace/sense, cardioversion/defibrillation electrodes or lead conductor(s), such as endocardial leads 125, 130. The endocardial leads 125, 130 are also electrically coupled to the connector header 115. The IMD 110 contains a battery and an operating system powered by the battery that may employ a microcomputer or a digital state machine for timing and controlling device functions in accordance with a programmed operating mode. The operating system includes memory registers in RAM for storing a variety of programmed-in operating mode and parameter values that are used by the operating system. The memory registers may also be used for storing data compiled from sensed cardiac activity and/or relating to device operating history or sensed physiologic parameters for telemetry out on receipt of a retrieval or interrogation instruction.

Information is communicated by RF transmissions between the IMD 110 and the external device 175. In one embodiment, the system uses short range RF downlink telemetry (DT) transmissions 185 and uplink telemetry (UT) transmissions 190. Programming commands or data are transmitted between the IMD RF telemetry antenna 180 and an external RF telemetry antenna 195 associated with the external device 175. In an uplink telemetry transmission 190, the external RF telemetry antenna 195 operates as a telemetry receiver antenna, and the IMD RF telemetry antenna 180 operates as a telemetry transmitter antenna. Conversely, in a downlink telemetry transmission 185, the external RF telemetry antenna 195 operates as a telemetry transmitter antenna, and the IMD RF telemetry antenna 180 operates as a telemetry receiver antenna.

Figure 3:
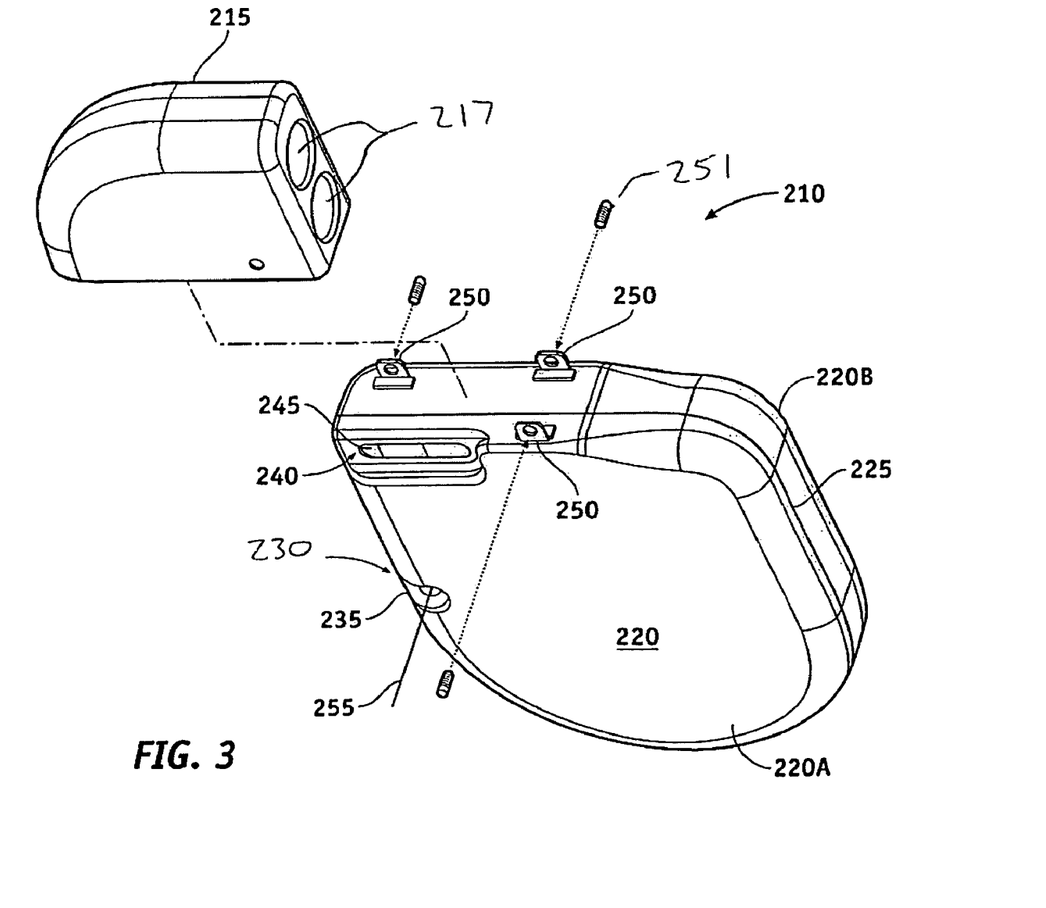
FIG. 3 is a simplified exploded perspective view showing the attachment of a connector header to the hermetically sealed housing.

FIG. 3 is a perspective view showing one embodiment of an IMD 210 that includes a connector header 215 and a hermetically sealed housing 220. One or more leads, such as leads 125, 130 described above, are adapted to be coupled to receptacles 217 of the connector header 215 in a manner known in the art. The hermetically sealed housing 220 is typically formed of a thin walled biocompatible material shaped in half sections, first shield 220a and second shield 220b, that are welded together in a seam 225. The housing 220 may be made of medical grade material, such as titanium, nickel-cobalt, gold, stainless steel, or any other such suitable medical grade material that is weldable. A telemetry recess 230 is formed in first side 220a that includes a telemetry feedthrough hole that a telemetry antenna feedthrough 235 is welded in. The telemetry antenna feedthrough may any suitable type, such as a coaxial antenna feedthrough. A connector recess 240 is formed in first side 220a that includes an elongated feedthrough hole that accommodates connector header feedthrough 245. Connector tabs 250 are positioned on the housing 220 for attachment of the connector header 215 with pins 251. An antenna 255, such as IMD RF telemetry antenna 180, shown in FIG. 1, is coupled to antenna feedthrough 235 by known means. In one embodiment, the antenna 255 is a separate antenna. In another embodiment, the antenna 255 is part of the connector header 215.

Figure 4:
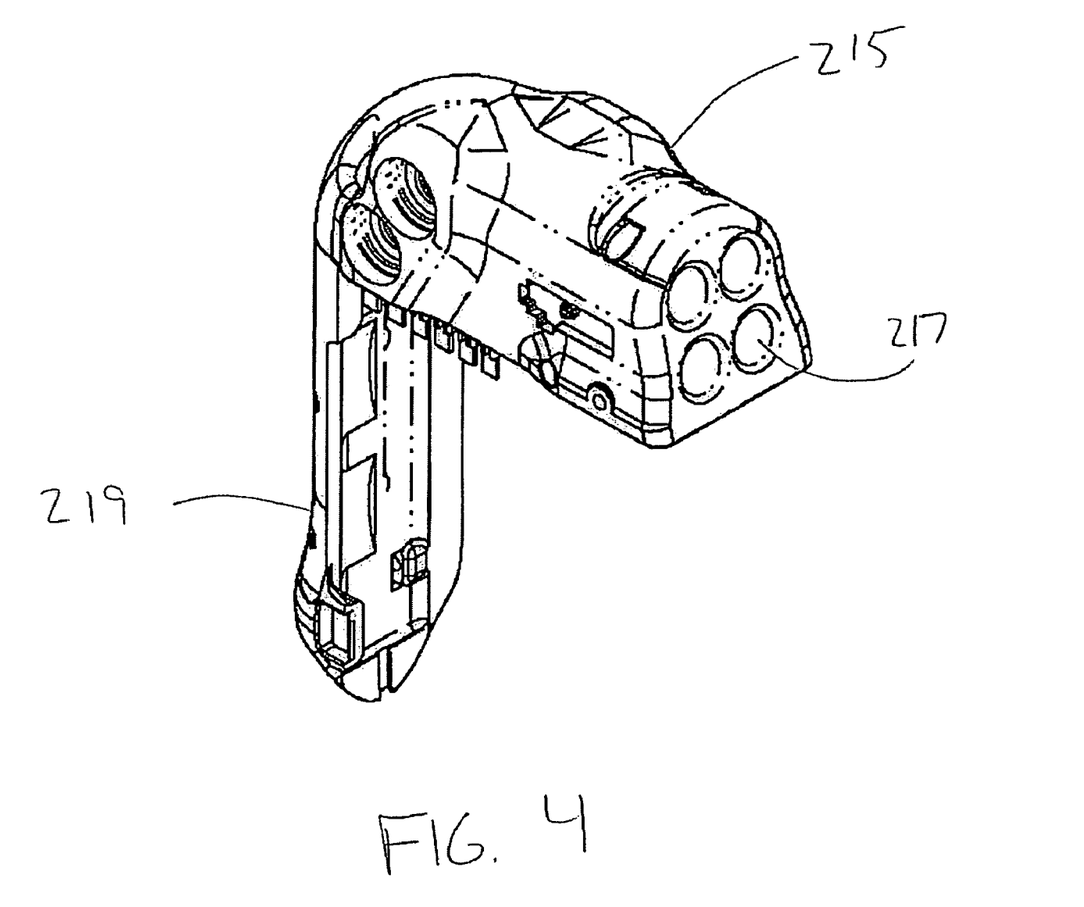
FIG. 4 is a perspective view showing an alternate embodiment of a connector header.

FIG. 4 is a perspective view showing an alternate embodiment of a connector header 215 having an extension portion 219. The extension portion 219 may house or cover an antenna.

Figure 5:
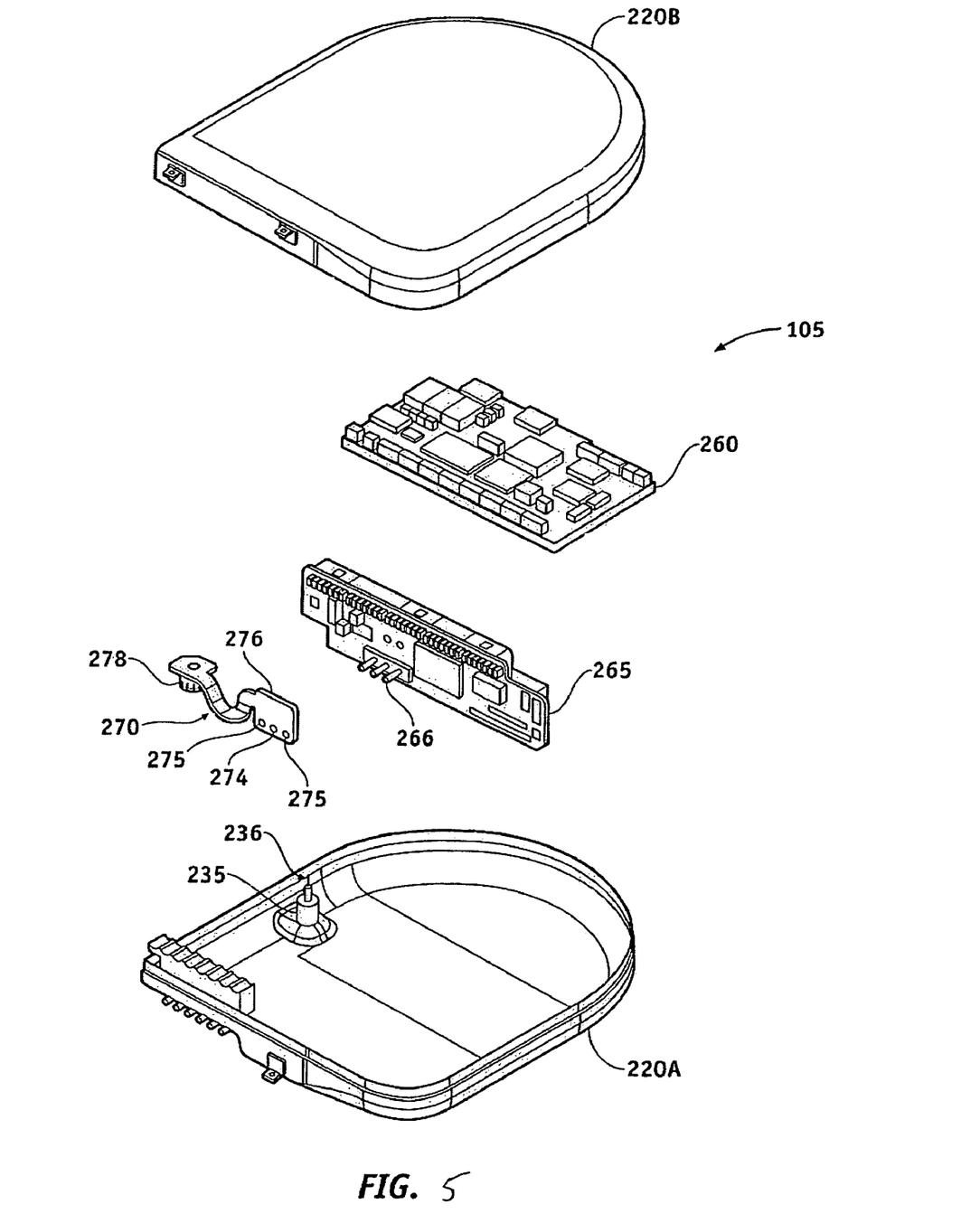
FIG. 5 is a simplified exploded perspective view of the hermetically sealed housing showing some of the internal components, including an RF module, an RF flexible circuit interconnect and an RF antenna feedthrough.

FIG. 5 shows an exploded perspective view of the hermetically sealed housing 220a and 220b shown in FIG. 3. In the embodiment shown, the internal components include a main circuit board 260, an RF module 265 and an RF antenna flexible circuit interconnect ("interconnect") 270. In one embodiment, the main circuit board 260 is electrically connected to the RF module 265 using connection techniques known to those skilled in the art. In another embodiment, the main circuit board 260 is electrically connected to the RF module 265 using unique connection titled Laser Ribbon Bond Pad Array Connector, disclosed in patent application Ser. No. 11/004,175 filed Dec. 3, 2004. In still another embodiment, the RF telemetry circuitry may be part of the main circuit board 260. Many of the components for the IMD are omitted for clarity and are known to those skilled in the art.

The interconnect 270 includes unique micro connectors that are designed to electrically couple to pins on the RF module 265 and the antenna feedthrough 235. The interconnect 270 is flexible such that the ends with the micro connectors may bend or twist to connect with the pins on the other components. In the embodiment shown, a first end of the interconnect 270 includes a spacer 276, a first antenna micro connector 274 and ground micro connectors 275 positioned in a first plane that align and mate with one or more pins 266 on the RF module 265. The pins 266 include an antenna pin and one or more ground pins. A second end of the interconnect 270 includes an antenna connector 278 having a second antenna micro connector 288 and a ground member 292 (see FIG. 8) that is in a second plane that align and mates with the antenna feedthrough 235.

Figure 6:
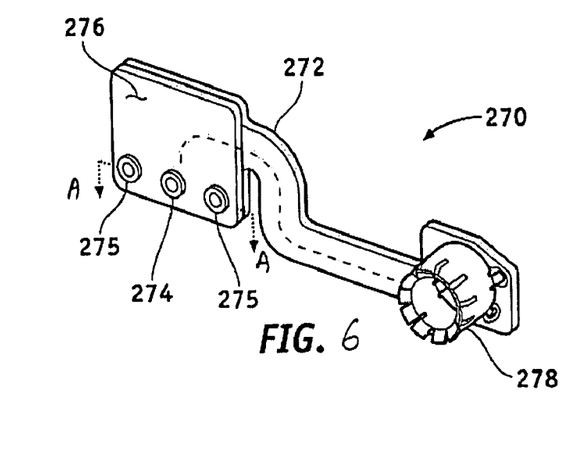
FIGS. 6 and 7 are perspective views of the RF flexible circuit interconnect.
Figure 7:
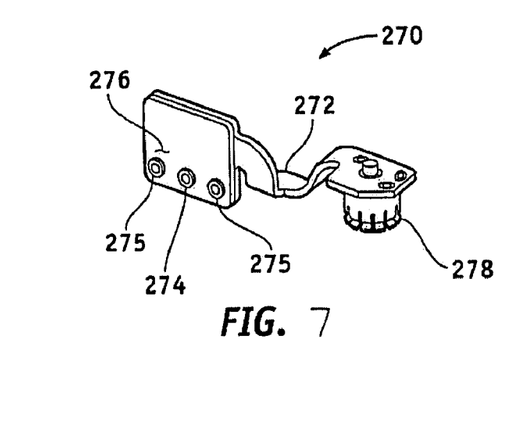

FIGS. 6 and 7 are perspective views of the interconnect 270 that includes a flexible body 272 having a first end with the first antenna micro connector 274, ground micro connectors 275 and a spacer 276, and a second end with the antenna connector 278. The flexible body 272 may be initially planer when assembled or fabricated, such as in FIG. 6, but has enough flexibility to be twisted when in use, such as in FIG. 7 (see also FIG. 5).

Figure 8:
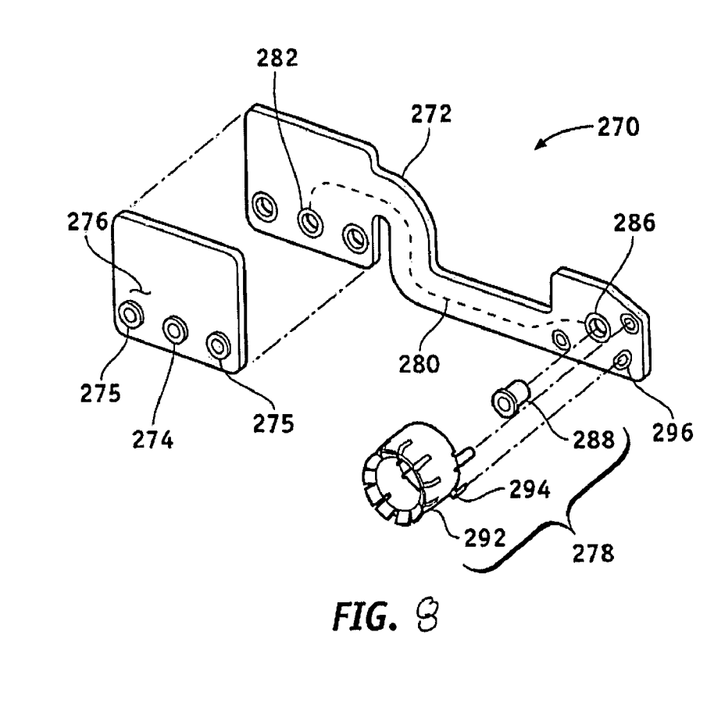
FIG. 8 is an exploded view of the RF flexible circuit interconnect shown in FIG. 6.

FIG. 8 is an exploded view of FIG. 6 showing more detail of the interconnect 270 components. The flexible body 272 includes an embedded controlled impedance strip line 280 having a first end 282 that can be electrically coupled to the first antenna micro connector 274 and a second end 286 that can be electrically coupled to a second antenna micro connector 288 of the antenna connector 278. The antenna connector 278 further includes a coaxial ground member 292 that is positioned around the second antenna micro connector 288 and attached to the flexible body 272 by known means, for example with tabs 294 inserted through openings 296. One or more ground micro connectors 275 and the coaxial ground member 292 are electrically coupled to the flexible body 272. The first antenna micro connector 274 and the ground micro connectors 275 may be attached to the spacer 276 (see FIG. 9).

The first antenna micro connector 274 and the ground micro connectors 275 are designed to electrically couple to pins on an RF module, such as the antenna and ground pins 266 on the RF module 265 shown in FIG. 5. The coaxial ground member 292 and second antenna micro connector 288 are designed to couple with an antenna feedthrough, such as coaxial antenna feedthrough 235 shown in FIG. 5. The antenna feedthrough 235 consists of two conductors that share a common axis. The inner conductor is an antenna pin 236 that couples with second antenna micro connector 288 and the outer conductor is a coaxial ground that ground member 292 slides over and couples with.

Figure 9:
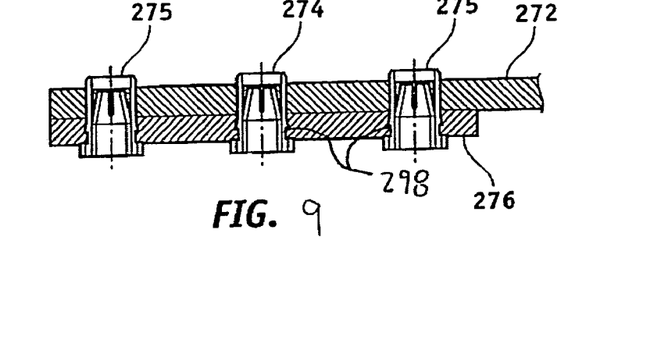
FIG. 9 is a cross-sectional view of the RF flexible circuit interconnect taken at A-A of FIG. 6.

FIG. 9 is a cross-sectional view taken at A-A of FIG. 6 showing the antenna micro connector 274 and ground micro connectors 275 attached to the flexible body 272 and spacer 276. The mirco connectors may be held to the spacer with a barb feature 298 in the micro connector 274, 275 housing (see also FIG. 10). The spacer 276 is attached to the flexible body 272 by known means, such as bonding. The micro connectors 274, 275 extend through the spacer 276 and mate with conductive through-holes in the flexible body 272, such that the antenna micro connector 274 is electrically coupled to a conductive through-hole of the embedded controlled impedance strip line 280 (not shown) and the ground micro connectors 275 are electrically coupled to a ground plane of the flexible body (not shown).

Figure 10:
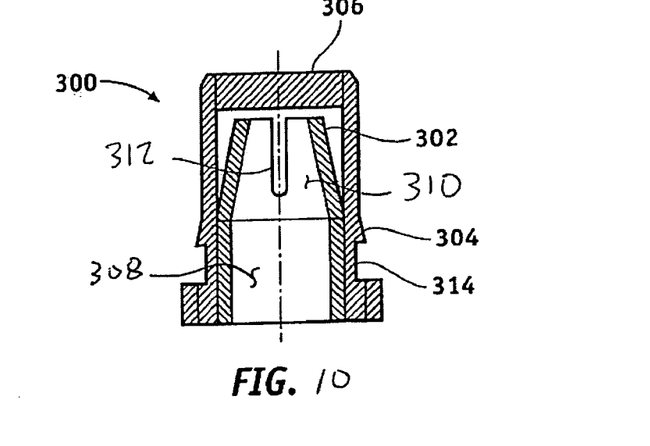
FIG. 10 is a cross-sectional view of one embodiment of a micro connector for use in the RF flexible circuit interconnect shown in FIG. 6.
Figure 11:
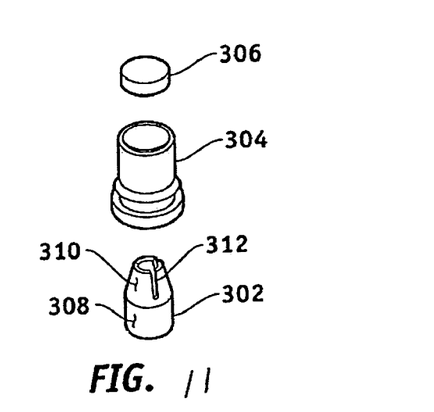
FIG. 11 shows an exploded perspective of the micro connector of FIG. 10.

FIG. 10 is a cross-sectional view showing one embodiment of a micro connector 300 for use in the present invention and FIG. 11 is an exploded perspective view showing the different components for the micro connector 300 of FIG. 10. One or more of the micro connector 300 embodiments may be used for antenna micro connectors 274, 288 and ground micro connectors 275, discussed above. One embodiment of the micro connector 300 is designed to electrically couple with the embedded controlled impedance strip line in the flexible body, such as embedded controlled impedance strip line 280 discussed above. Another embodiment of the micro connector 300 is designed to electrically couple to the ground plane of the flexible body. The embodiments of the micro connector 300 are also designed to electrically couple to pins on an RF module and a central pin of an antenna feedthrough, such as pins 266 and feedthrough pin 236 discussed above.

The micro connector 300 includes a central contact socket 302, a cylindrical housing 304 and a plug 306. The central contact socket 302 includes a cylindrical body portion 308 at a proximal end that is dimensioned to press-fit into the housing 304. While a press-fit embodiment is disclosed for joining the central contact socket 302 into the cylindrical body portion 308, other embodiments are contemplated, such as latching embodiments and clearance fit embodiments, and all embodiments may be soldered or welded together.

The internal diameter of the cylindrical body portion 308 is dimensioned to allow insertion of a pin (such as pin 236 and/or pin 266). The central contact socket 302 also includes a plurality of inward bending finger-contacts 310 separated by slots 312 at a distal end. The finger-contacts 310 are designed to contact and flex when a pin is inserted between them. The number of finger-contacts 310 and the inward bending angles may vary for the different embodiments, depending on the pin size to be inserted.

The central contact socket 302 and the housing 304 are made of electrically conductive material, and are designed to withstand high voltages, such as during defibrillation shocks. In one embodiment, the central contact socket 302 is made of beryllium copper alloy with a finish of gold over nickel. In another embodiment, the housing 304 is made of brass alloy covered with a finish of tin/lead over nickel. The plug 306 is dimensioned to be inserted in the end of the housing and to seal the housing opening opposite the central contact socket 302. The plug 306 may be removable and may be made of an organic fiber. In some embodiments, the micro connector 300 may also include a barb 314 in the housing 304 to assist in assembly, such as with the spacer 276.

Figure 12:
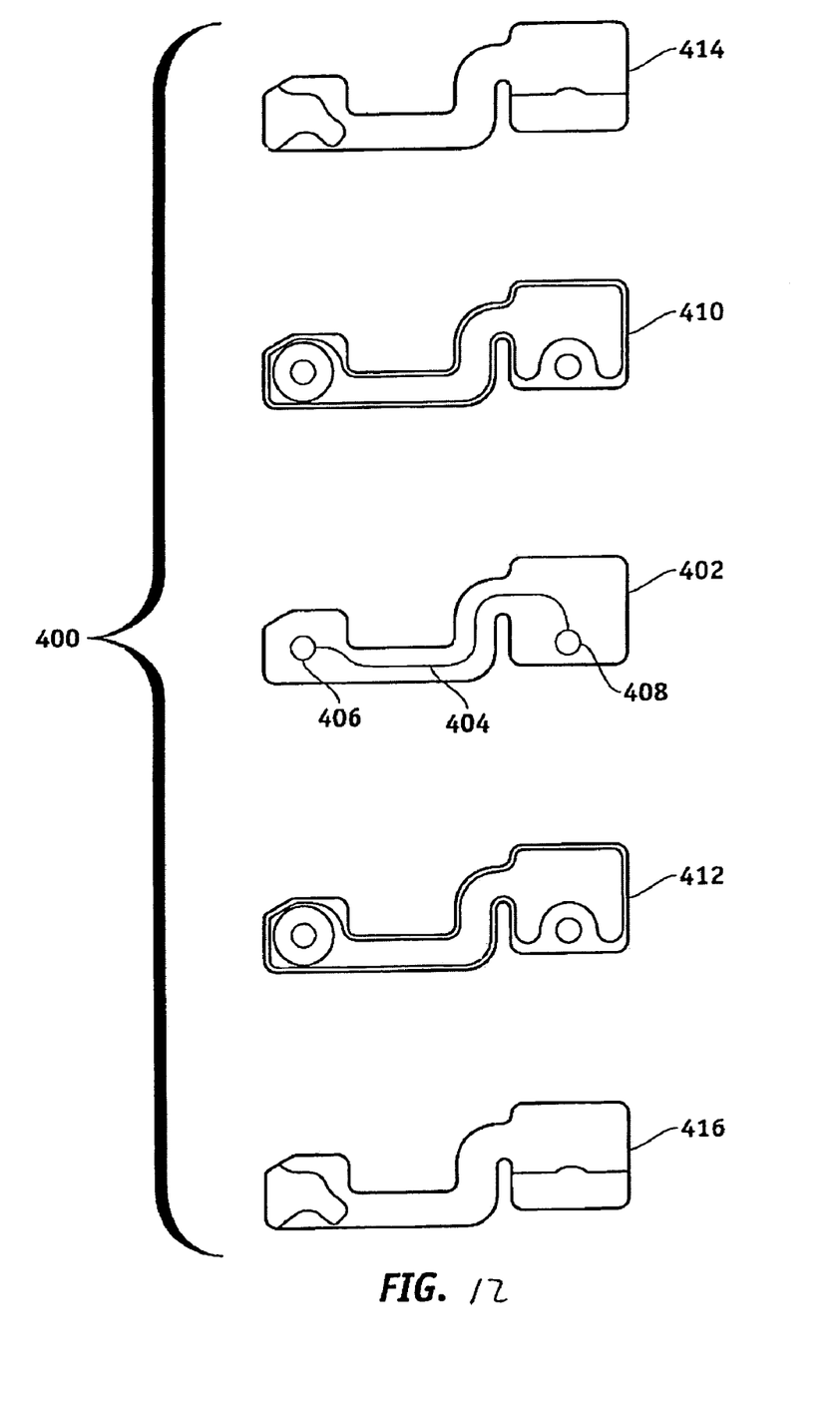
FIG. 12 is an exploded view showing one embodiment of a flexible body for use in the RF flexible circuit interconnect shown in FIG. 6.

FIG. 12 is an exploded view showing one embodiment of a flexible body 400 having an embedded controlled impedance strip line used in an interconnect, such as interconnect 270 shown in FIG. 6 and discussed above. In the embodiment shown, the flexible body 400 is a layered structure with a central or middle layer 402 having a controlled impedance strip line 404 terminating in first and second conductive through-holes 406, 408. The conductive through-holes 406, 408 are sized to mate with the micro connectors 300 discussed above. The controlled impedance strip line 404 is electrically conductive and provides a proper impedance match to a coaxial cable, such as through telemetry antenna feedthrough 435. The controlled impedance strip line 404 may be fabricated by known means, such as deposition, plating or screening, on the central layer 402. Shielding or grounding layers 410, 412 are positioned on both sides of the middle layer 402, covering the impedance strip line 404, to provide EMI shielding. The shielding layers are also electrically conductive and made of a conductive material, such as copper. Cover or insulating layers 414, 416 are placed over the shielding layers 410, 412. The cover layers 414, 416 may be made of an electrically insulating material, such as polyimide.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A radio frequency (RF) flexible circuit interconnect, comprising:
   a planar flexible body with an RF transmission line embedded therein, the transmission line having a first end and a second end;
   a first antenna micro connector electrically coupled to the first end of the RF transmission line and a second antenna micro connector electrically coupled to the second end of the RF transmission line, wherein the first antenna micro connector being configured to electrically couple with an antenna pin of an RF module, and the second antenna micro connector being configured to electrically couple with an antenna feedthrough.

2. The interconnect of claim 1, further comprising a ground member electrically coupled to the RF transmission line, wherein the ground member being configured to electrically couple with an antenna feedthrough.

3. The interconnect of claim 1, wherein the ground member is positioned proximate the second antenna micro connector.

4. The interconnect of claim 1, wherein the planer flexible body is a layered structure comprising:
   a central layer made of electrically conductive material, the central layer having a first side and a second side;
   a controlled impedance strip line positioned on the first side of the central layer;
   a first ground layer made of electrically conductive material covering the first side of the central layer;
   a second ground layers made of electrically conductive material covering the second side of the central layer;
   a first cover layer made of electrically insulating material covering the first grounding layer; and
   a second cover layer made of electrically insulating material covering the second grounding layer.

5. The interconnect of claim 1, wherein each of the first and second antenna micro connectors comprises:
   an antenna micro connector housing; and
   an antenna central contact socket securely positioned in the antenna micro connector housing, the antenna central contact socket having a body portion.

6. The interconnect of claim 5, wherein the central contact socket is configured to engage an inserted pin.

7. The interconnect of claim 5, wherein the central contact socket further includes a plurality of inward bending finger-contacts.

8. The interconnect of claim 7, wherein the inward bending finger-contacts are flexible with resilient properties.

9. The interconnect of claim 5, wherein the antenna micro connector housing is a first electrically conductive material and the central contact socket is a second electrically conductive material.

10. The interconnect of claim 9, wherein the first electrically conductive material is brass alloy.

11. The interconnect of claim 10, wherein the first electrically conductive material further includes a finish of tin/lead over nickel.

12. The interconnect of claim 9, wherein the second electrically conductive material is beryllium copper alloy.

13. The interconnect of claim 12, wherein the second electrically conductive material further includes a finish of gold over nickel.

14. The interconnect of claim 1, wherein the RF transmission line includes a signal line and a ground plane, the first and second antenna micro connectors being electrically coupled to the signal line.

15. The interconnect of claim 14, wherein the signal line is a controlled impedance strip line.

16. The interconnect of claim 1, further comprising one or more ground micro connectors electrically coupled to the RF transmission line.

17. The interconnect of claim 16, wherein each of the one or more ground micro connectors comprises:
   a ground micro connector housing; and
   a ground central contact socket securely positioned in the ground micro connector housing, the ground central contact socket having a body portion.

18. The interconnect of claim 17, wherein the ground central contact socket is configured to engage an inserted pin.

19. The interconnect of claim 17, wherein the ground central contact socket further includes a plurality of inward bending finger-contacts.

20. The interconnect of claim 19, wherein the inward bending finger-contacts are flexible with resilient properties.

* * * * *